United States Patent [19]

Nadeau et al.

[11] Patent Number: 5,840,487
[45] Date of Patent: *Nov. 24, 1998

[54] INTERNAL CONTROLS FOR ISOTHERMAL NUCLEIC ACID AMPLIFICATION REACTIONS

[75] Inventors: James G. Nadeau, Chapel Hill; Michael C. Little, Raleigh, both of N.C.

[73] Assignee: Becton, Dickinson and Company, Franklin Lakes, N.J.

[*] Notice: The term of this patent shall not extend beyond the expiration date of Pat. No. 5,457,024.

[21] Appl. No.: 801,542

[22] Filed: Feb. 18, 1997

Related U.S. Application Data

[63] Continuation of Ser. No. 508,006, Jul. 2, 1995, abandoned, which is a continuation of Ser. No. 58,648, May 5, 1993, Pat. No. 5,457,027.

[51] Int. Cl.[6] .............................. C12Q 1/68; C12P 19/34
[52] U.S. Cl. ................................................ 435/6; 435/91.2
[58] Field of Search ........................................ 435/6, 91.2

[56] References Cited

U.S. PATENT DOCUMENTS 5,219,727  6/1993  Wang et al. .
5,457,027  10/1995  Nadeau et al. .............................. 435/6

OTHER PUBLICATIONS

Guatelli et al PNAS 87:1874–1878 (1990).
Mathews (Anal Biochem. 169:1–25 (1988).
Eisenach et al (America Res. Dis 144:1160–1163 (1991)).
Thierry et al (Nucleic Acid Res 18:188 (1990).

*Primary Examiner*—Eggerton A. Campbell
*Attorney, Agent, or Firm*—Donna R. Fugit

[57] ABSTRACT

Methods employing internal oligonucleotide standards in isothermal nucleic acid amplification reactions to determine the efficacy of the amplification reaction and to quantify pre-amplification target levels.

10 Claims, 5 Drawing Sheets

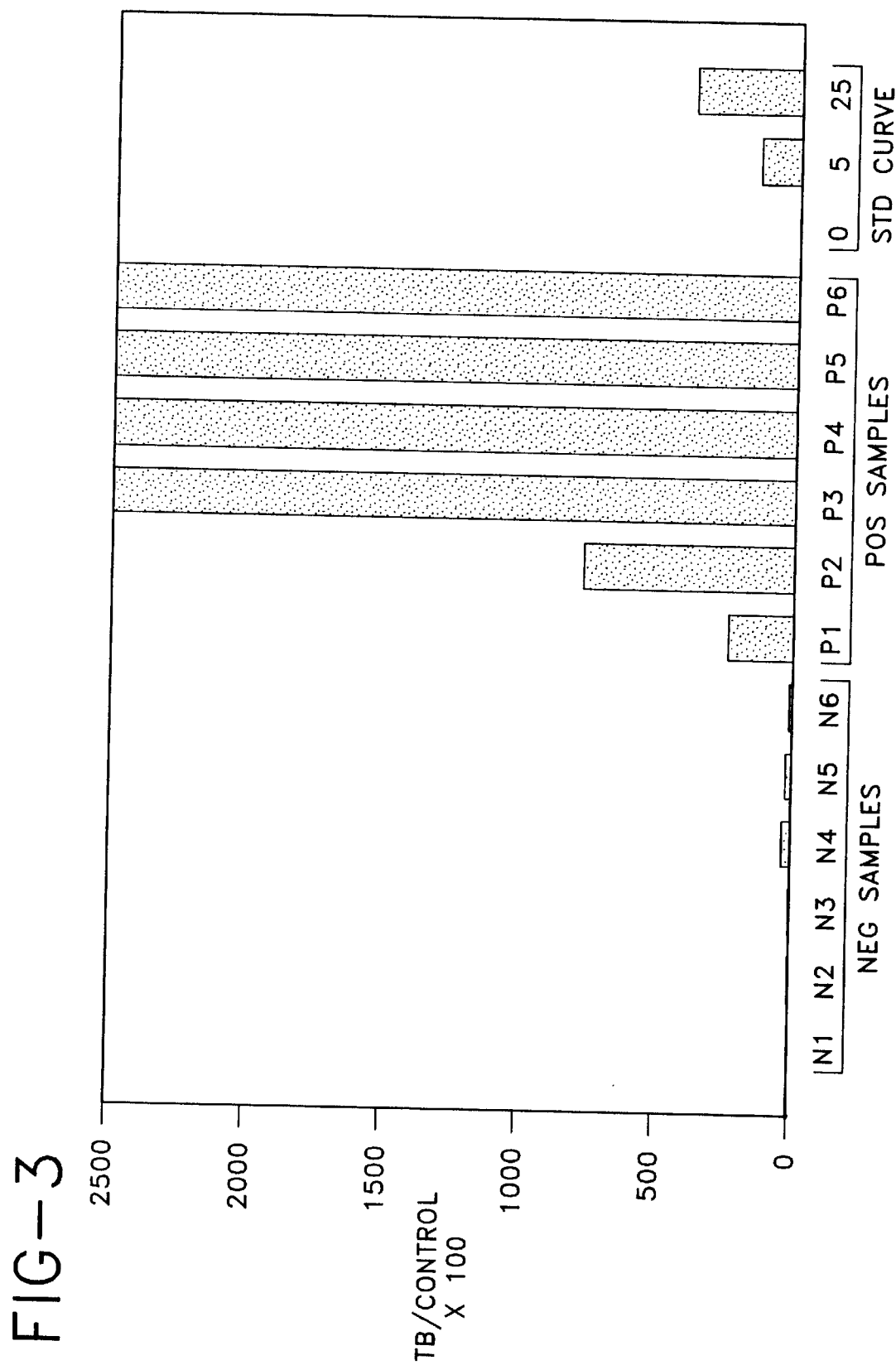

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ACTGAGATCC  CCTAGCGACG  ATGTCTGAGG  CAACTAGCAA  AGCTGGTCGA  GTACGCC         5 7
```

( 2 ) INFORMATION FOR SEQ ID NO:2:

( i ) SEQUENCE CHARACTERISTICS:
        ( A ) LENGTH: 52 base pairs
        ( B ) TYPE: nucleic acid (C) STRANDEDNESS: double
(D) TOPOLOGY: linear (i i) MOLECULE TYPE: DNA (genomic)

(v i) ORIGINAL SOURCE:
 (A) ORGANISM: Mycobacterium tuberculosis (x i) SEQUENCE DESCRIPTION: SEQ ID NO:2:

ACTGAGATCC CCTATCCGTA TGGTGGATAA CGTCTTTCAG GTCGAGTACG CC 52

(2) INFORMATION FOR SEQ ID NO:3:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (x i) SEQUENCE DESCRIPTION: SEQ ID NO:3:

GCTTTGCTAG TTGCC 15

(2) INFORMATION FOR SEQ ID NO:4:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (i x) FEATURE:
  (A) NAME/KEY: misc_feature
  (B) LOCATION: 1
  (D) OTHER INFORMATION: /standard_name= "5'Biotin label"
   / label= 5'-BBB- (x i) SEQUENCE DESCRIPTION: SEQ ID NO:4:

GCTTTGCTAG TTGCC 15

(2) INFORMATION FOR SEQ ID NO:5:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (i x) FEATURE:
  (A) NAME/KEY: misc_feature
  (B) LOCATION: 15
  (D) OTHER INFORMATION: /standard_name= "3'amine
   conjugated to alkaline phosphatase"
   / label= -al2-AP-3'

(x i) SEQUENCE DESCRIPTION: SEQ ID NO:5:

TCAGACATCG TCGCT 15

(2) INFORMATION FOR SEQ ID NO:6:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (i x) FEATURE:
  (A) NAME/KEY: misc_feature
  (B) LOCATION: 1
  (D) OTHER INFORMATION: /standard_name= "5'Biotin label"
   / label= 5'-BBB- (x i) SEQUENCE DESCRIPTION: SEQ ID NO:6:

CCTGAAAGAC GTTAT                                                                    15

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 16
        (D) OTHER INFORMATION: /phenotype="3'AMINE CONJUGATED TO
            ALKALINE PHOSPHATASE"
            / label= -am-AP-3'

(xi) SEQUENCE DESCRIPTION: SEQ ID NO:7:

CCACCATACG GATAGT                                                                   16

INTERNAL CONTROLS FOR ISOTHERMAL NUCLEIC ACID AMPLIFICATION REACTIONS

This application is a continuation of application Ser. No. 08/508,006, filed Jul. 27, 1995, abandoned which is a continuation of application Ser. No. 08/058,648, filed May 5, 1993, (U.S. Pat. No. 5,547,027).

FIELD OF THE INVENTION

The present invention relates to methods for isothermal in vitro nucleic acid amplification, and in particular to methods for assessing the amplification activity of a sample or quantitating the amount of a target sequence present in a sample.

BACKGROUND OF THE INVENTION

In vitro nucleic acid amplification techniques have provided powerful tools for detection and analysis of small amounts of nucleic acids. The extreme sensitivity of such methods has lead to attempts to develop them for diagnosis of infectious and genetic diseases. Nucleic acid amplification techniques can be grouped according to the temperature requirements of the procedure. The polymerase chain reaction (PCR; R. K. Saiki, et al. 1985. *Science* 230, 1350–1354), ligase chain reaction (LCR; D. Y. Wu, et al. 1989. *Genomics* 4, 560–569; K. Barringer, et al. 1990. *Gene* 89, 117–122; F. Barany. 1991. *Proc. Natl. Acad. Sci. USA* 88, 189–193) and transcription-based amplification (D. Y. Kwoh, et al. 1989. *Proc. Natl. Acad. Sci. USA* 86, 1173–1177) require temperature cycling. In contrast, methods such as strand displacement amplification (SDA; G. T. Walker, et al. 1992. *Proc. Natl. Acad. Sci. USA* 89, 392–396; G. T. Walker, et al. 1992. *Nuc. Acids. Res.* 20, 1691–1696), self-sustained sequence replication (3SR; J. C. Guatelli, et al. 1990. *Proc. Natl. Acad Sci. USA* 87, 1874–1878) and the Qβ replicase system (P. M. Lizardi, et al. 1988. *BioTechnology* 6, 1197–1202) are isothermal reactions. In addition, WO 90/10064 and WO 91/03573 describe use of the bacteriophage phi29 replication origin for isothermal replication of nucleic acids.

In general, these nucleic acid amplification techniques have been used to produce qualitative results in diagnostic assays. There is, however, a great deal of interest in developing quantitative nucleic acid amplification methods and methods for determining the amplification activity (i.e., efficacy) of a sample. These capabilities would provide improved reliability and precision to nucleic acid-based amplification diagnostic assays.

Because, in many cases, nucleic acid amplification is an exponential process, quantitation of the absolute amount of a specific target by coamplification of an internal control sequence has been difficult. For this reason, small differences in the efficiency of amplification of the control and target sequences can result in large differences in the yield of amplification products and erroneous quantitative comparisons. Coamplification of internal control sequences has been used in PCR to quantitate the amount of target sequence present in a sample. It has been recognized for several years that the accuracy of this method depends on the ability to select an internal control sequence which will exhibit the same amplification efficiency as the target sequence. Initially, coamplification techniques employed target and control sequences which were amplified by different PCR primer pairs, making it difficult to balance amplification efficiencies and reducing the accuracy of the method. For example, J. Chelly, et al. ((1988) *Nature* 333, 858–860) reported coamplification of aldolase A reporter mRNA and dystrophin mRNA in human tissues. Although the absolute amount of dystrophin mRNA could not be directly determined, the method allowed the relative amount to be estimated by comparing the aldolase A amplification product with the dystrophin amplification product. An estimate of the amount of dystrophin target mRNA as a percentage of total mRNA was obtained using published figures estimating the percentage of aldolase A mRNA. These authors therefore employed an internal control sequence unrelated to the target sequence and the two sequences were coamplified using different primer pairs. In addition, the amplification products of the control and target sequences were of different sizes.

Improvements in PCR internal control have been reported by selecting internal control sequences which can be amplified using the same primers as the target sequence. See, for example, WO 93/02215 and WO 92/11273. In certain studies, it has been recommended that the target and control sequences be of different lengths to facilitate their identification on gels (K. D. Eisenach, et al. 1991. *Amer. Rev. Resp. Dis.* 144, 1160–1163; A. M. Wang, et al. 1989. *Proc. Natl. Acad. Sci.* 86, 9717–9721; International Patent Application No. WO 91/02817). G. Gilliland, et al. (1989. *J Cell. Biochem.* 13, Suppl. E., 270; (1990) *Proc. Natl. Acad. Sci. USA* 87, 2725–2729) describe competitive PCR reactions in which internal control sequences are approximately the same size as the target and are primed using the same primers. Although Gilliland, et al. teach that the target and control sequences should be closely related to reduce the number of variables, length of the amplified sequence is not described as one of the variables which significantly affects amplification efficiency, as the rate of PCR is known to be relatively unaffected by the length of the target.

Publications relating to internal control of PCR reactions describe the variables which should be controlled to ensure equal amplification efficiencies between the target and control sequences. These include, in part, the length and nucleotide sequence of the primer pairs, the concentrations of polymerase, dNTPs, $MgCl_2$, nucleic acid templates and primers, the rate of primer-dimer formation, melting temperatures of the nucleic acids, and concentration and length of nucleic acid templates. See WO 91/02817 and Gilliland, et al., supra. While the importance of balancing amplification efficiencies and the variables involved have been appreciated in PCR, factors affecting amplification rates (and therefore the selection of appropriate control sequences) in isothermal systems such as SDA are expected to be significantly different from those affecting PCR.

One significantly different characteristic of PCR resides in the three steps comprising a single amplification cycle: (1) thermal denaturation of double-stranded target nucleic acid, (2) hybridization of primers to the now single-stranded target, and (3) extension of the hybridized primers to form an identical copy of the double stranded target which was denatured in step (1). In PCR, these steps are synchronized such that only one of the steps can occur at any given time. When one step is finished, the next can begin only after a change in reaction temperature. One complete cycle therefore requires several temperature changes. Thus, PCR amplification proceeds in coherent phases in which all target molecules are undergoing the same step of the process at the same time. The efficiency with which a given target is amplified is directly dependent on the combined efficiencies of the three component steps.

When two or more target sequences are co-amplified by PCR, the amplification efficiency of each sequence is similarly the product of the efficiencies for the component steps. Therefore, for two non-identical sequences to be amplified with equal efficiency in PCR each component step need only be equally complete for the two sequences at the end of the time allotted for that step. It is not necessary that a given reaction (e.g., primer extension) occur at the same rate for both targets. It is only necessary that the reactions occur to the same extent before the entire reaction is shifted to the next step of the cycle (e.g., denaturation). Thus, the rates of reaction of the two targets may be slightly different at any given step, provided sufficient time is allowed for completion of the slower reaction prior to initiating the next reaction step. As a result, in PCR the overall amplification efficiency for two targets can be made identical even if the rates of their fundamental molecular processes (i.e., the reaction rates of the component steps of the cycle) are different merely by adjusting the thermal cycling routine. The amplification properties of the two target sequences need not be exquisitely well-balanced for an equal degree of amplification to occur.

This is not the case in isothermal systems such as SDA, in which amplification does not proceed in coherent phases. While amplification of each target molecule does occur through a concerted series of reactions in such systems, at any given point in time, different individual target molecules will be in different phases of the amplification cycle. In such continuous amplification systems it is not possible to delay reaction steps for one target sequence to allow lagging reactions involving a second target sequence to catch up. Instead, an imbalance in fundamental rates of reaction for the two target sequences, regardless of how small, translates directly into a difference in amplification efficiencies. As previously noted, even small differences in amplification efficiencies result in large differences in product yield in exponential amplification systems such as PCR and SDA. Small reaction rate imbalances are therefore magnified in isothermal amplification systems such as SDA, whereas similar imbalances in PCR may be effectively negated by the choice of an appropriate temperature cycling routine. For these reasons, choosing control sequences with appropriately balanced amplification efficiencies is more critical and more difficult in isothermal systems than in systems which are performed in discrete reaction steps. For example, the efficiency of SDA decreases with increasing length of the target or control sequence above about 60 nucleotides. In contrast, PCR targets differing in length by hundreds of nucleotides can be amplified with similar efficiencies. The lower amplification temperature of SDA and other isothermal amplification reactions also allows an increased degree of secondary structure in the primers and the target sequences, which in turn affects the rate of the amplification reaction.

EP 0 525 882 describes a method for quantifying a target nucleic acid in a Nucleic Acid Sequence Based Amplification (NASBA) reaction by competitive amplification of the target nucleic acid and a mutant sequence. The method is performed with a fixed amount of sample and a dilution series of mutant sequence. The analysis is performed by determining the amount of added mutant sequence which reduces the signal from the target sequence by 50%, i.e., the point at which the mutant sequence and target sequence are present in equal amounts. To produce accurate quantification, the amplification reactions described in EP 0 525 882 must be allowed to continue until at least one of the reagents is essentially exhausted, i.e., into the post-exponential phase of the reaction where competition for limited reagents can occur. Furthermore, the calculations are accurate only when two reactions are competing for reagents—the target amplification and the mutant sequence amplification. The results are therefore not reliable when a third reaction, such as background amplification, is occurring. As essentially all amplification reactions include some degree of background amplification, the EP 0 525 882 quantifying method is only accurate for a high level of target sequence. At low target levels, competing background amplification reactions would significantly interfere with the accuracy of the calculations. Because it relies on amplifying various dilutions of the mutant sequence with the target, the EP 0 525 882 method is also susceptible to tube-to-tube variations in the amount of mutant and target sequence. Even small differences in the amount of target sequence or slight inaccuracies in the dilutions of mutant sequence between tubes are exponentially amplified in the subsequent amplification reaction and are reflected in the quantification calculations. In contrast, the present method does not require competition for between control and target sequences for reagents or that the reaction go into the post-exponential phase. It is accurate in both the exponential and post-exponential phases of the amplification reaction. The ratio of target/control sequence in the present method is therefore not adversely affected by background amplification reactions which may be occurring and remains the same regardless of the extent of background reaction. The result can therefore be obtained earlier in the amplification reaction and variability is reduced by the use of a single target/control co-amplification reaction rather than a series of reactions.

Applicants have, for the first time, provided methods for deducing pre-amplification target levels from the quantity of amplification product generated during an isothermal nucleic acid amplification reaction which are essentially independent of interference from background. These methods are useful for verifying that individual amplification reactions possess sufficient amplification activity to enable detection of a specified minimum number of target molecules (i.e., sample efficacy) as well as for quantitating the amount of target initially present. These methods have been made possible by the Applicants' discovery of reaction variables which must be controlled to balance the amplification rates for control and target sequences in isothermal amplification reactions. Like other amplification processes, the exponential nature of SDA and other isothermal reactions causes a small change in amplification rate to produce large differences in the number of target copies generated. Amplification rate and efficiency are known to be sensitive to a variety of experimental parameters, including temperature, ionic strength and the level of non-target DNA present. Consequently, small variations in these (and other) parameters can result in dramatically different yields of amplified target from nominally identical samples. This sample-to-sample variation can make quantification of initial target levels very difficult and can also result in erroneous diagnoses if low amplification activity leads to a false conclusion that no target was present in the sample.

All reaction parameters which contributed to variability in amplification rates in isothermal reactions were not previously known, however. Further, control of such variables and balancing of amplification rates is more critical and more difficult for isothermal amplification methods because their continuous nature does not permit the opportunity to adjust for small imbalances the way PCR does (see above). Consequently, small differences in reaction rates can make quantitation of initial target levels very inaccurate and can result in erroneous conclusions if low amplification activity leads to a false conclusion that no target nucleic acid is present in the sample.

SUMMARY OF THE INVENTION

The present invention provides methods for the use of internal oligonucleotide standards in isothermal nucleic acid amplification reactions to 1) determine the efficacy of the amplification reaction and 2) to quantify pre-amplification target levels. As the internal control sequence is amplified in the same reaction mixture as the target sequence, variables such as ionic strength, level of non-target nucleic acid and temperature are constants. It has now been discovered that to balance the amplification rates of target and control sequences in isothermal amplification reactions, the target and control sequences should be substantially the same length and have substantially the same G+C content. It is not necessary that the sequences be closely related at the nucleotide sequence level other than in G+C content. This provides an internal control sequence with melting characteristics similar to the target sequence. Further, is have been found that the internal control sequence should be selected to have minimal secondary structure at the amplification temperature.

DESCRIPTION OF THE DRAWINGS

FIG. 2A shows analysis of samples which were clinically negative by culturing. FIG. 2B shows analysis of samples which were clinically positive by culturing.

FIG. 3 illustrates the use of the target/control sequence ratio to correct for inhibition of amplification in clinical samples, aiding in correct interpretation of the results.

DETAILED DESCRIPTION OF THE INVENTION

Figure 1:
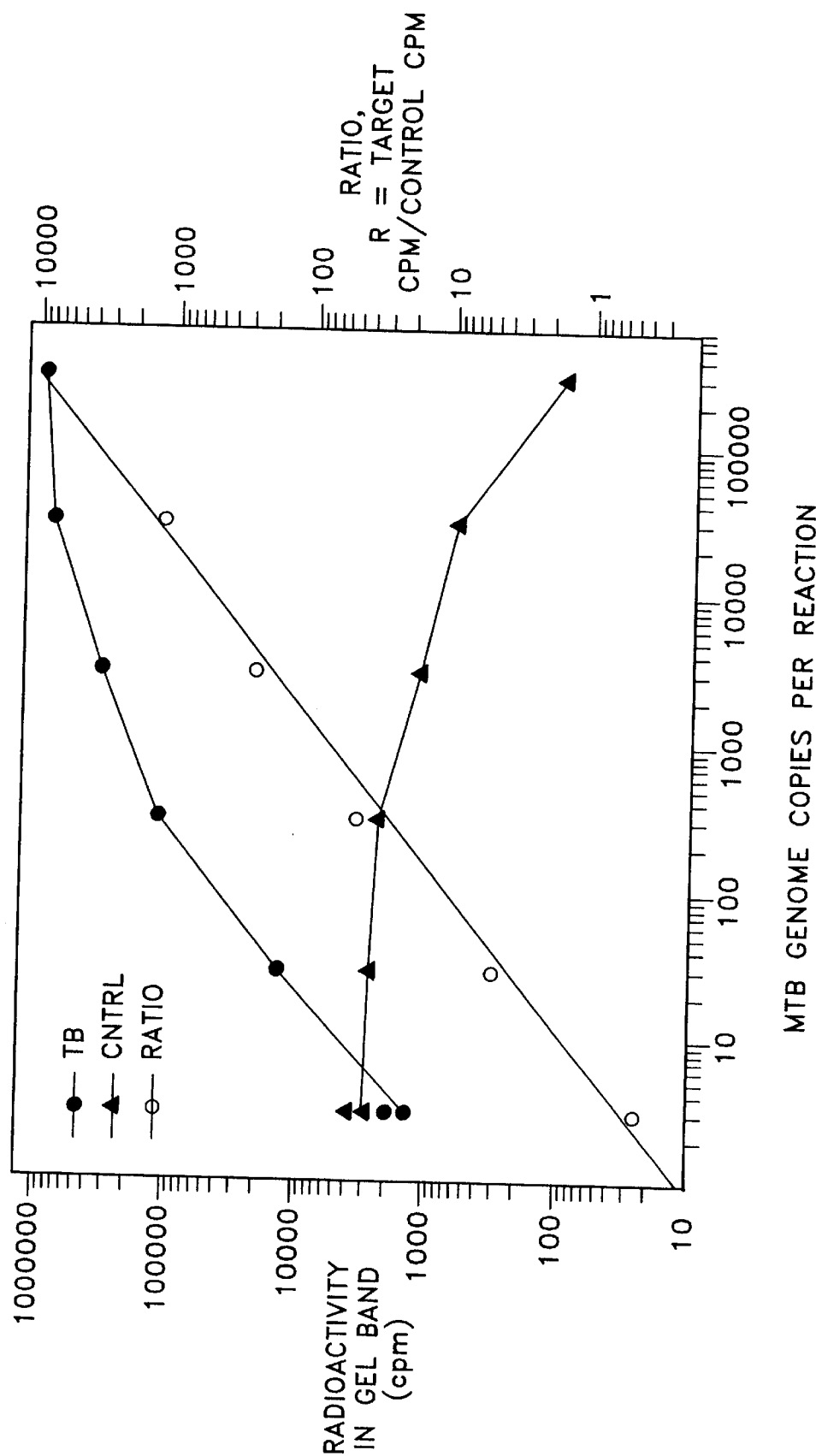
FIG. 1 illustrates co-amplification of an internal control sequence and a fragment of the IS6110 sequence of *Mycobacteria tuberculosis*.

The present invention relates to the use of oligonucleotides as internal standards or controls in isothermal nucleic acid amplification reactions 1) to determine the efficacy of individual amplification reactions and 2) to quantify pre-amplification target levels. The internal control oligonucleotide also provides a means for identifying "false negative" results, as an absence of amplified control sequence in a sample which is also negative for amplified target sequence suggests a failure of the amplification reaction rather than absence of the target sequence. The number of target copies generated during a given amplification reaction depends both on the quantity of target present prior to amplification and on the overall efficiency and rate of the amplification reaction itself. The methods of the invention provide means for evaluating the amplification activity of individual reaction mixtures, independent of the presence or absence of target molecules in the sample. A known quantity of an internal control oligonucleotide is added to each mixture and this molecule is co-amplified with the target sequence, if present. The internal control sequence is selected so that its rate of amplification under a standard set of reaction conditions is closely matched to the rate of amplification of the target sequence. In this way, the ratio of control concentration to target concentration remains constant throughout the amplification reaction. The quantity of target sequence initially present may then be calculated from the ratio of target and control levels after amplification and the known amount of control sequence added.

For reliability, the amplification rates of the control and target sequences should be as similar as possible. This is preferably accomplished in isothermal amplification reactions by selecting a control sequence which can be amplified by the same primers used to amplify the target sequence. Use of a single set of primers also reduces the level of nonspecific background amplification reaction which may be encountered when multiple primer sets are used in a single amplification reaction. To achieve similar amplification rates, it is also preferred that the control sequence be selected so as to have minimal secondary structure (and therefore minimal folding) and a length similar to the target sequence. In addition, the internal region of the control sequence (between the primer binding sites) is preferably sufficiently different from the target sequence to allow the two molecules to be distinguished by hybridization of oligonucleotide probes. The target and control sequence should preferably, however, have roughly equivalent G+C content so that hybridization and melting characteristics are similar.

The internal control oligonucleotide may be chemically synthesized, amplified from a cloned sequence or isolated according to other means known in the art. For convenience, the oligonucleotide is preferably synthesized using any of the known methods for synthesis of defined nucleic acid sequences. See, for example, C. Caruthers, et al. 1982. *Cold Spring Harbour Symp. Quant. Biol.* 47, 411–418; Adams, et al. 1983. *J Am. Chem. Soc.* 105, 601; Froehler, et al. 1986. *Nuc. Acids Res.* 14, 5399; Narang, et al. 1979. *Methods Enz.* 68, 90; Ogilvie, et al. 1988. *PNAS* 85, 5764. Following production of the internal control sequence for a selected target sequence according to the parameters described above, the control sequence is added in a known amount to an isothermal nucleic acid amplification reaction, for example SDA, 3SR or Qβ replicase amplification. SDA is preferred for use with the internal controls described herein. The amount of control sequence added to the reaction will depend on the length of time the amplification will be allowed to run and the estimated rate of reaction. The dynamic range of the control sequence for a given amount of target sequence is very broad (e.g., up to at least 100,000 molecules of control sequence for amplification of 50 Mtb genomes). To ensure that an accurately detectable amount of amplified control sequence will be produced in a given amplification reaction, dilutions of the reaction mixture containing a range of control concentrations, may be prepared and run in parallel in a manner similar to the procedure described by Gilliland, et al. (1989 and 1990), supra, for competitive PCR. Alternatively, the control sequence may be added to a single reaction in a single amount if the degree of amplification expected can be estimated.

Following amplification, the levels of target and control sequence produced may be determined by any of the methods known in the art for detecting specific nucleic acid sequences. For example, the amplification products may be detected by hybridization to oligonucleotide probes tagged with a detectable label, one probe specifically hybridizing to the control sequence and another probe specifically hybridizing to the target sequence. If the target-specific and control-specific probes are hybridized simultaneously to the amplification products, the labels should be separately identifiable to facilitate distinguishing the respective amounts of control and target. Otherwise, separate aliquots of the amplification reaction may be separately hybridized to target-specific and control-specific probes tagged with the same label. The detectable label may be conjugated to the probe after it is synthesized or it may be incorporated into the probe during synthesis, for example in the form of a label-derivatized nucleotide. Such labels are known in the art and include directly and indirectly detectable labels. Directly detectable labels produce a signal without further chemical reaction and include such labels as fluorochromes, radioisotopes and dyes. Indirectly detectable labels require further chemical reaction or addition of reagents to produce the detectable signal. These include, for example, enzymes such as horseradish peroxidase and alkaline phosphatase, ligands such as biotin which are detected by binding to label-conjugated avidin, and chemiluminescent molecules. The probes may be hybridized to their respective amplification products in solution, on gels, or on solid supports. Following hybridization, the signals from the associated labels are developed, detected and separately quantitated using methods appropriate for the selected label and hybridization protocol. The amount of signal detected for each amplification product is a reflection of the amount present.

One preferred method for detecting the target and control amplification products is by polymerase extension of a primer specifically hybridized to the target or control sequence. The primer is labeled as described above, preferably with a radioisotope, so that the label of the primer is incorporated into the extended reaction product. This method is described in more detail by Walker, et al. (1992) *Nuc. Acids Res.* and *PNAS*, supra.

Another preferred method for detecting amplified target and control sequences is a chemiluminescent method in which amplified products are detected using a biotiniylated capture oligodeoxynucleotide probe and an enzyme-conjugated detector oligodeoxynucleotide probe. After hybridization of these two probes to different sites on an amplified target sequence, the complex is captured on a streptavidin-coated microtiter plate, and the chemiluminescent signal is developed and read in a luminometer. This detection method can be performed in less than two hours and is sensitive enough to detect as few as one pre-amplification target sequence.

When the inventive methods are used to quantitate starting levels of target sequence, the post-amplification levels of target and control are determined by means of a signal generating method, and the ratio of target-specific/control-specific signal levels (R) is calculated. This ratio (R=target signal/control signal) is found to vary linearly with the ratio of target/control starting concentrations (i.e., concentrations before amplification). This linear relationship has been shown to hold over a 100,000 fold range of initial target/control ratios. In principle, the concentration of target present at time=0 may be determined by comparing the post-amplification target to control signal ratio R against a standard plot of R versus starting Mtb levels.

When the inventive methods are used to determine sample efficacy, the amount of control sequence added to the reaction mixture will generally be selected to represent a minimum number of target molecules which would be detectable in a positive sample. In this way, the control sequence acts as a control for the amplification reaction itself, as detectable amplification of a control sequence present in a quantity at the lower threshold of sensitivity of the reaction serves to corroborate a negative result for the target sequence. Inability to detect amplification of the control sequence alerts the practitioner to the fact that the sample may not be truly negative, but may only appear negative due to failure of the amplification reaction.

A particularly preferred control oligonucleotide sequence (SEQ ID NO: 1) for use in amplification reactions for detection of *Mycobacterium tuberculosis* (Mtb) is as follows: 5'ACTGAGATCCCCTAGCGACGATGTCT-GAGGCAACTAGCAAAGCTGGTCGAGTACGCC 3'. This oligonucleotide is matched in control-target combination with the Mtb target sequence derived from nucleotides 972–1023 of the IS6110 insertion sequence (SEQ ID NO:2): 5'ACTGAGATCCCCTATCCGTATGGTG-GATAACGTCTTTCAGGTCGAGTACGCC 3'.

EXAMPLE 1

Co-amplification of the above internal control sequence and Mtb target sequence was carried out by means of SDA under the conditions described by Walker, et al. (1992), supra with the following modifications. Each 50 $\mu$L reaction mixture contained 30,000 copies of the single stranded control sequence molecule (SEQ ID NO: 1) and genomic Mtb DNA present in concentrations ranging from 0 to 300,000 copies per reaction. Each reaction mixture also contained 50 mM potassium phosphate (pH 7.4), 6 mM magnesium chloride, 0.1 mg bovine serum albumin, 12% glycerol (v/v), 250 ng human placental DNA (Sigma Chemical Co., St. Louis, Mo.), 150 units HincII (New England Biolabs, Beverly, Mass.) and 2.5 units of exo⁻ Klenow DNA polymerase (United States Biochemical Corp., Cleveland, Ohio). The reactions also contained the $S_1$, $S_2$, $B_1$ and $B_2$ oligodeoxyribonucleotide primers described by Walker, et al. (500 nM $S_1$ and $S_2$, 50 nM $B_1$ and $B_2$).

All components of the amplification reactions except HincII and exo⁻ Klenow were combined and the mixture was heated to 95° C. for two minutes to denature the double stranded target DNA. After cooling to 39° C. (3–5 min.), the HincII and exo⁻ Klenow polymerase were added and the mixtures were kept at 39° C. for 2 hr. before amplification was terminated by heating to 95° C. for two minutes. After cooling, the $^{32}$-P primer extension method described by Walker, et al., supra, was used to assay 3.8 $\mu$L aliquots of each reaction for the presence of either amplified target or control molecules. For target detection, the $^{32}$-P labelled probe described by Walker, et al., supra, was used. For detection of the control sequence, the following probe was used: 5'-$^{32}$P-GCTTTGCTAGTTGCC-3' (SEQ ID NO:3). Components of the primer extension reaction were separated by polyacrylamide gel electrophoresis, and bands corresponding to target or control specific extension products were cut from the gel and quantified by liquid scintillation counting of $^{32}$-P radioactive decay.

FIG. 1 displays the radioactivity measured from each band (in counts per minute) plotted against the number of Mtb genome copies present in the mixture before amplification. This plot demonstrates the efficient co-amplification of target and control sequences over a broad ($10^5$-fold) range of initial Mtb levels. Furthermore, the target-signal/control-signal ratio is linear across the entire range of pre-amplification Mtb levels. The pre-amplification level of Mtb DNA present in a sample may be determined by (i) adding a known quantity of the control molecule to the sample before amplification, (ii) co-amplifying the target and control sequences by means of SDA, (iii) determining the ratio of target/control-specific signal levels, and (iv) using a standard curve, such as the ratio (R) versus Mtb genome plot in FIG. 1, to assess pre-amplification target levels from the post-amplification ratio of target-specific/control-specific signal levels.

EXAMPLE 2

Clinical samples of patient sputum designated as positive or negative for *M. tuberculosis* by culture were processed as follows. To the sample of sputum was added an equal volume of liquification reagent (potassium hydroxide/N-acetyl cysteine). the mixture was mixed briefly on a vortex mixer and centrifuged at 4,000×g for 15 min. The supernatant was decanted and the pellet was washed twice with 25 mM $KPO_4$, pH 7.6. The pellet from these washings was brought to 500 µL with the same buffer and autoclaved. The autoclaved sample was assayed in a standard SDA reaction of 50 µL total using 25 µL of the clinical sample. Included in the reaction was 10,000 molecules of synthetic internal control sequence (SEQ ID NO:1). After amplification for 2 hr. at 37° C., the reaction was stopped by heating at 95° C. for 2 min. and split for the independent detection of products from IS6110 (Mtb) and internal control amplification.

Amplification products were detected in a chemiluminescent assay. Oligonucleotide capture probes were synthesized using a DNA synthesizer (Model 380B, Applied Biosystems, Foster City, Calif.) and BIOTIN-ON Phosphoramidite (Clonetech, Palo Alto, Calif.). This resulted in three biotin residues at the 5' terminus of the capture probe. The capture probe for the control sequence (SEQ ID NO:4) was 5'-GCTTTGCTAGTTGCC-3' and the capture probe for the Mtb IS6110 target sequence (SEQ ID NO:6) was 5'-CCTGAAAGACGTTAT-3'. The olignocleotides were purified by reverse phase High Pressure Liquid Chromatography (HPLC) (Brownlee Lab Aquapore RP 300 Column—220×4.6 mm, C8 column, 7 particle, 300 Å pore size) with a UV monitor at 254 nm and a gradient of 14–44% Buffer B in Buffer A over one hour (Buffer B: 0.1M triethylamine-acetate, pH 7 with 50% acetonitrile; Buffer A: 0.1M triethylamine-acetate, pH 7) and a flow rate of 1 ml/min.

The oligodeoxynucleotide detector probes were synthesized using the Model 380B DNA synthesizer and a 3'-amino-modifier-C3 column (Glenn Research, Sterling, Va.). This produced oligonucleotides with a 3' amine terminus for subsequent conjugation to alkaline phosphatase. The detector probe for the control sequence (SEQ ID NO:5) was 5'-TCAGACATCGTCGCT-$al_2$-AP-3' ($al_2$=amino link 2). The detector probe for the IS6110 target sequence (SEQ ID NO:7) was 5'-CCACCATACGGATAGT-am-AP-3' (am= amino modifier). Calf intestine alkaline phosphatase (AP) (EIA grade, Boehringer Mannheim, Indianapolis, Id.) was dialyzed overnight at 4° C. against 50 mM potassium phosphate pH 7.5 and subsequently centrifuged to remove aggregates. Four ml of 10 mg/ml AP was combined with 40 µl of 50 mM succinimidyl-4-(p-maleimidophenyl) butyrate (SMPB) (Pierce, Rockford, Ill.) dissolved in N,N'-dimethylformamide (DMF) (Aldrich, Milwaukee, Wis.) and allowed to react in the dark at room temperature for 30 min. The derivatized AP and excess SMPB were separated using a NAP-25 column (Pharmacia) and 50 mM potassium phosphate pH 7.5 (degassed and purged with $N_2$). The absorbances of the NAP-25 column fractions were read at 260 and 280 nm and the void volume peak was pooled. The concentration of derivatized alkaline phosphatase was determined by absorbance at 280 nm using an extinction coefficient of 0 m75 ml/µmole $cm^{-1}$. The derivatized AP obtained was stored on ice less than two hours until conjugation to the derivatized oligodeoxynucleotides.

Fifty nmoles of oligodeoxynucleotide was diluted in 13.4 µl 1M potassium phosphate pH 7.2 and mixed with 28.8 µl of 50 mM n-succinimidyl-3-(2-pyridyldithio)propionate (SPDP) Pierce, Rockford, Ill.) diluted in DMF. This mixture was incubated in the dark for 1 hr. at room temperature. Dithiothreitol (DTT) was diluted in 50 mM potassium phosphate pH 7.5 to a concentration of 1M and added to the oligodeoxynucleotide/DMF mixture to a final concentation of 0.1M and allowed to incubate for 15 min. at room temperature. Excess DTT and SPDP were separated from the derivatized oligodeoxynucleotide by elution over a NAP-25 column with 50 mM potassium phosphate pH 7.5 (degassed and purged with $N_2$). The derivatized oligodeoxynucleotide eluted in the void volume as judged by absorbance at 160 and 180 nm. The reduced oligodeoxynucleotide, in order to avoid oxidation, was reacted with the derivatized AP within 10 min. The derivatized oligodeoxynucleotide and derivatized AP were incubated 1–4 hrs. at room temperature and then overnight at 4° C. The solution was quenched using 1/100th volume of 50 mM beta-mercaptoethanol in 50 mM potassium phosphate pH 7.5. The crude conjugate was concentrated according to the manufacturer's instructions using CENTRIPREP 30 (Amicon) to approximately 2 ml using 20 mM Tris pH 7.5. The crude conjugate was purified by HPLC using a DEAE-5PW column (7.5 mm×7.5 cm) and a gradient of 0 to 66% Buffer B in Buffer A (Buffer B: 20 mM Tris, 1M NaCl pH 7.5; Buffer A: 20 mM Tris pH 7.5) and a flow rate of 1 ml/min. Absorbance was monitored at 254 nm. The absorbance at $A_{260}$ and $A_{280}$ nm were taken using a spectrophotometer and the fractions with $A_{260}/A_{280}$ equal to 1 were pooled. The protein concentration of the conjugated oligodeoxynucleotide was determined (BCA Protein Assay Kit, Pierce, Rockford, Ill.).

The activity of the alkaline phosphatase(AP) detector oligodeoxynucleotide probes was determined as follows. The conjugate was diluted to 5 µg/ml in 50 mM Tris-HCl, 100 mM NaCl, 1 mM $MgCl_2$, 1 mg/ml BSA, pH 7.5. The substrate, 4-nitrophenylphosphate (pNPP), at a concentration of 5 mM, was prepared in 1M diethanolamine, 1 mM $MgCl_2$, pH 9.8. AP activity was assayed as follows, at 25° C. The conjugate (5 µl) was pipetted into 2 ml of the substrate solution and the change in absorbance was monitored at 405 nm. The initial rate was calculated from the linear region, and the reaction rate (µmole product/minute) was calculated using the extinction coefficient of the product p-nitrophenol at 405 nm as equal to 18500 $M^{-1}cm^{-1}$. The specific activity of the AP detector oligodeoxynucleotide was calculated in µmole/minute/mg. The AP detector probe was diluted to 2 µM in 20 mM Tris pH 7.5, 1M NaCl, 50 µg/ml sonicated salmon sperm DNA, 0.05% sodium azide, and stored thereafter at 4° C. The 20 mM Tris, pH 7.5, 1M NaCl buffer was autoclaved before addition of the other components.

Coated microtiter plates for capture of the target/probe complexes were prepared as follows. Biotinylated bovine serum albumin (biotin*BSA) (Pierce, Rockford, Ill.) was diluted to 5 µg/ml in 0.3M glycine pH 9.6 (prepared using autoclaved water) and was pipetted into each well (200 µl/well) of a MICROLITE1 plate (Dynatech, Chantilly, Va.). The plates were incubated at 4° C. overnight and washed twice (375 µl/wash) using FTA hemagglutination buffer (Becton Dickinson Microbiology Systems) pH 7.2 prepared using autoclaved water. Streptavidin (50 µ g/ml) (BRL, Bethesda, Md.) in hemagglutination buffer was added to the biotin*BSA coated microtiter wells (100 µl/well). Plates were covered and incubated for 1 hr. at 37° C. Unbound streptavidin was discarded by inversion and manual shaking. Blocking buffer (300 µl/well) (hemagglutination buffer pH 7.2, 0.05% w/v bovine serum albumin) was then added. The plates were covered and incubated 30 min. at 37° C. The blocking buffer was discarded by inversion and manual shaking. Plates were washed twice with hemagglutination buffer (375 µl/well), then once using hemagglutination buffer with 2% w/v trehalose (375 µl/well) (Fluka, Ronkonkoma, N.Y.). Plates were vigorously tapped dry manually and then dried for approximately 4 hr. under vacuum at ≦0.5 Torr at 25° C., sealed in mylar pouches with desiccant, and stored overnight at room temperature prior to use. The plates were stored thereafter at 2°–8° C.

SDA reactions (50 μl) in microcentrifuge tubes were mixed with 5 μl of 1 mg/ml carrier DNA (sheared by sonication) (salmon sperm, Sigma, St. Louis, Mo.). The samples were heated for 5 min. at 95° C. to denature DNA and allowed to cool at room temperature for 5 min. Forty-five μl of hybridization mixture (0.5M sodium phosphate pH 7, 0.1% w/v bovine serum albumin (Sigma, St. Louis, Mo.), 2 pmole biotinylated capture oligodeoxynucleotide probe, and 0.5–1 pmole AP detector oligodeoxynucleotide probe was added per sample for a final volume of 100 μ l. The samples were incubated for 5 min. at 37° C. to hybridize DNA. Individual samples were added to each coated microtiter plate well, covered, and incubated for 30 min. at 37° C. Three stringency washes (300 μl/well) (10 mM sodium phosphate pH 7, 0.1% w/v bovine serum albumin, 0.05% v/v NONIDET 40) were performed at room temperature. Each wash was allowed to remain in the microtiter wells for 1 min. before removing. LUMIPHOS 530 (100 μl) (Lumigen, Inc., Detroit, Mich.) substrate was added, and the plates were covered and incubated for 30 min. at 37° C. Luminescence was read in Relative Light Units (RLU) on a microtiter plate luminometer (Labsystems, Research Triangle Park, N.C.) at 37° C., using a 2 sec./well integration time.

Figure 2A:
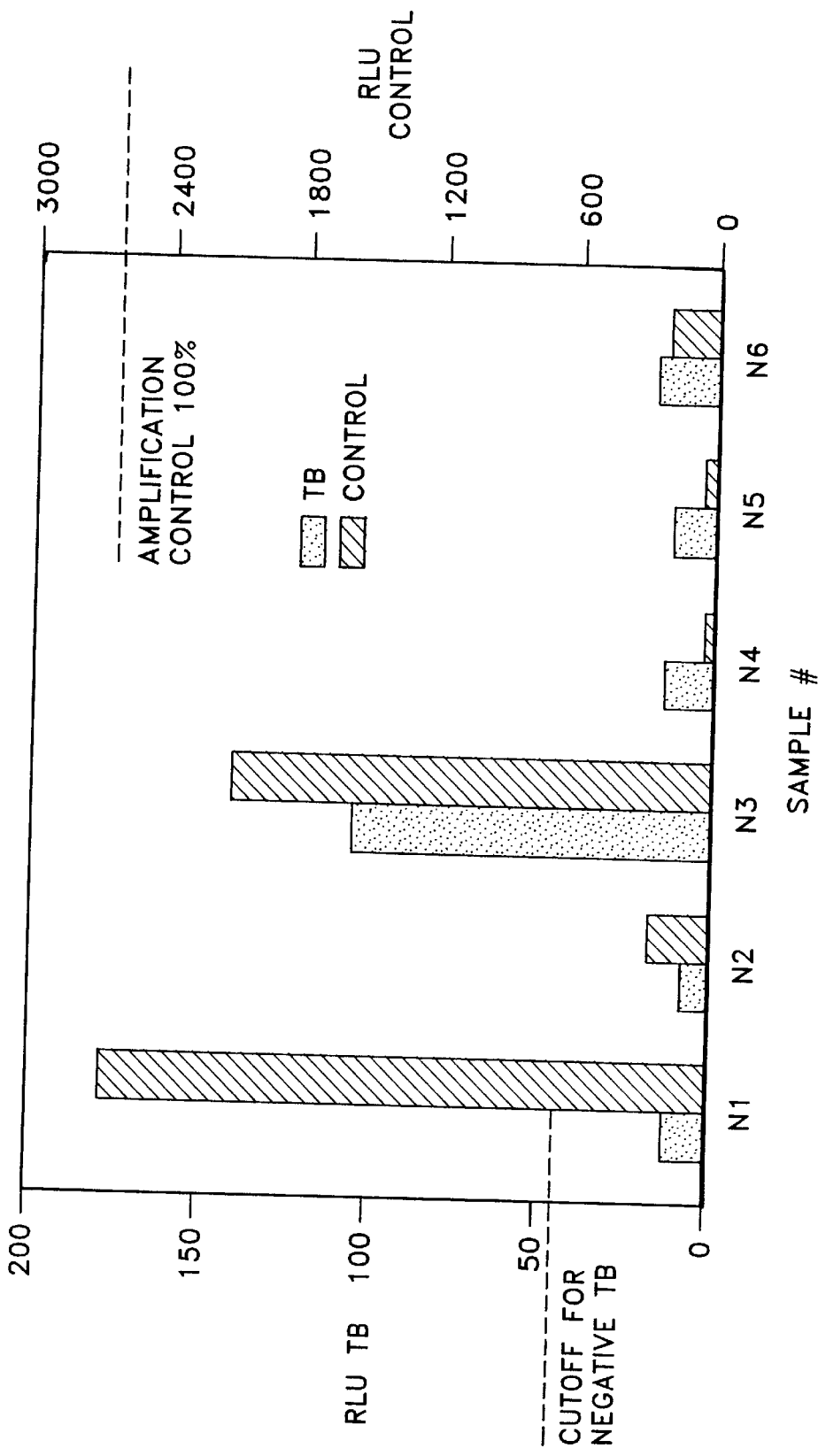
FIGS. 2A–2B illustrates the advantages of including internal control sequences in isothermic nucleic acid amplifications of clinical samples as controls for detecting inhibition of amplification and identifying "false negatives".

FIG. 2A presents the RLU results for six individual clinically negative samples for both Mtb (TB) and the internal control (Control) amplification products. The dashed line on the "RLU TB" axis indicates the RLU from the standard curve when no Mtb target sequence was present. This value (less than 50 RLU) would be expected if the sample were negative. The dashed line on the "RLU Control" axis indicates the value for the internal control sequence if there is no inhibition of the amplification reaction. Only one of the negative samples (N1) shows no inhibition of internal control sequence amplification. The corresponding TB signal from this sample is below the zero value from the standard curve, indicating that this sample is truly negative for M. tuberculosis. Each of the remaining samples (but in particular N2, N4, N5 and N6) show inhibition of the internal control as well as low TB values. In the absence of the internal control, these samples might erroneously be considered TB negative by a DNA probe test. The internal control sequence thus allows false negatives to be avoided. As about 95% of clinical samples are negative for TB, the value of this internal control for allowing the practitioner to discard true negatives is significant.

Figure 2B:
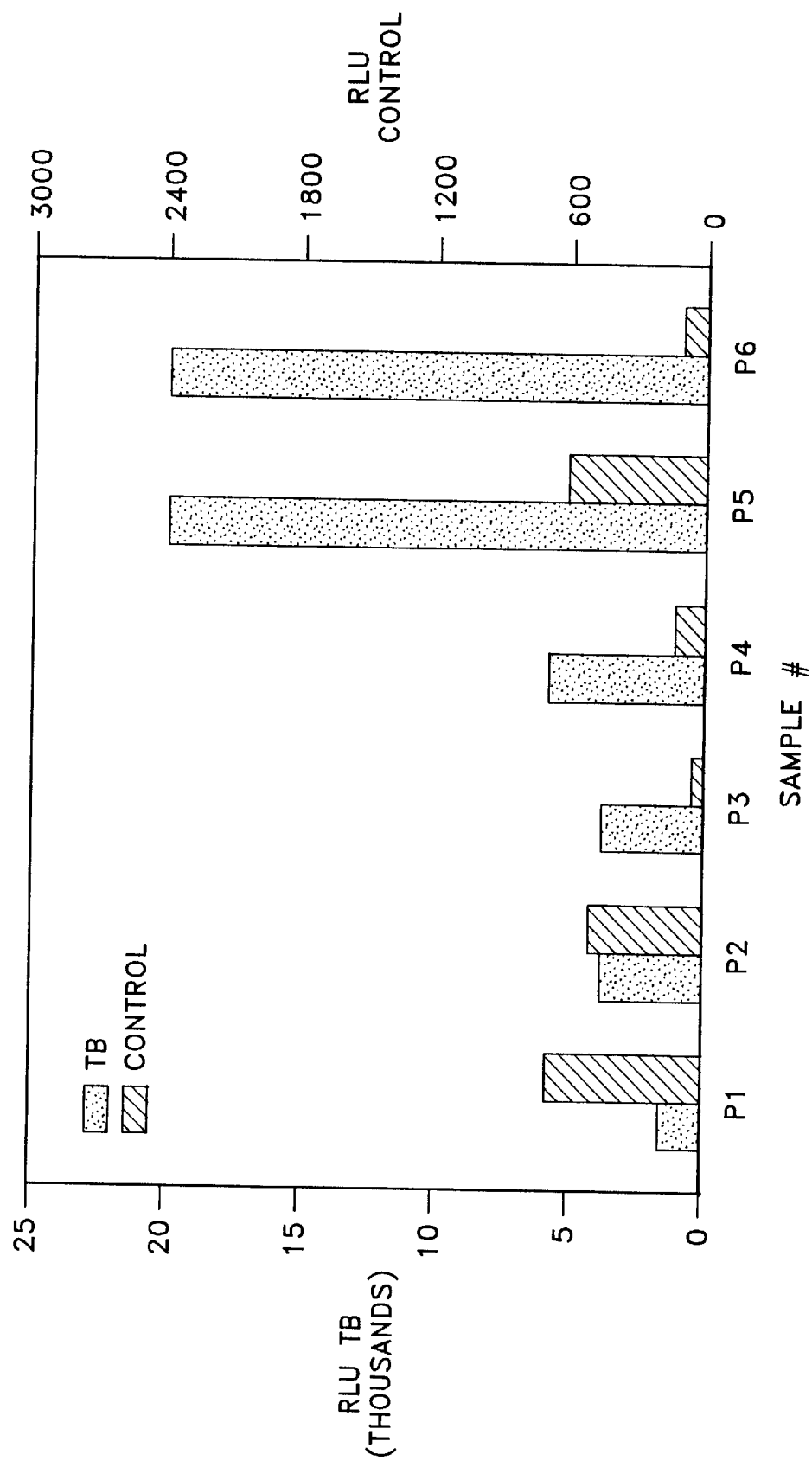

FIG. 2B presents similar results for a set of positive clinical samples. Each of the samples shows some inhibition of internal control amplification. However, even the TB signals for the sample with the lowest RLU (1600 RLU, P1) are well above the zero value (about 50 RLU), allowing rapid confirmation of these samples as positive.

FIG. 3 illustrates use of the TB/control signal ratio of the samples in FIG. 2A and FIG. 2B to compensate or correct the results for amplification inhibition. Samples which have a high TB/control ratio are true positives and those which have a low ratio are true negatives. The appropriate minimum ratio for positivity is determined from a standard curve generated by coamplifying a series of known amounts of target sequence (including no target sequence) with a constant amount of control sequence. The standard curve may also be used to quantify the amount of target sequence initially present in the sample.

EXAMPLE 3

Figure 4:
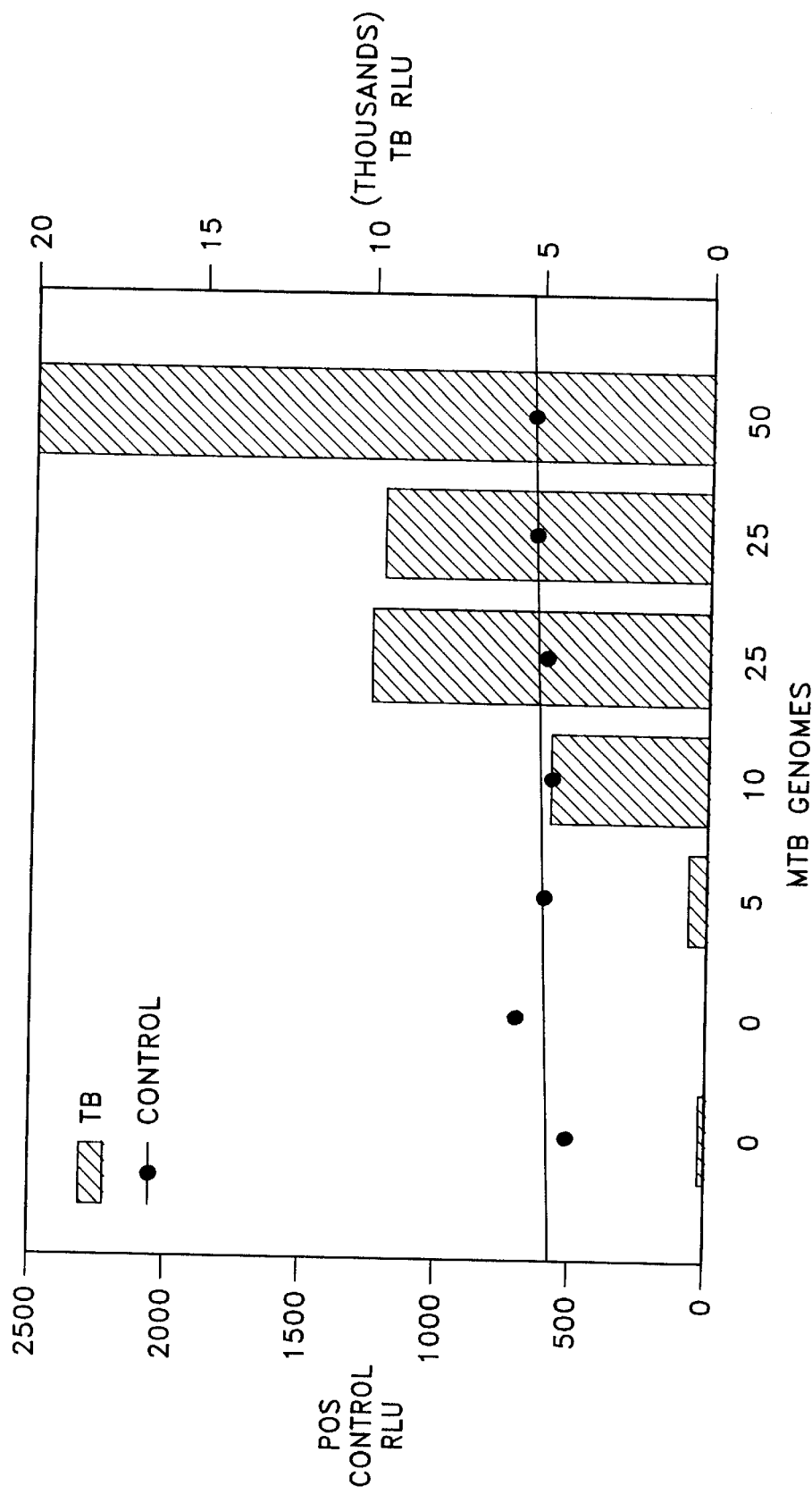
FIG. 4 illustrates the consistency of amplification of a constant amount of control sequence in the presence of varying amounts of target sequence.

The internal control sequence was co-amplified with various levels of M. tuberculosis genomic DNA. Samples of 0, 5, 10, 25 or 50 genomic copies of purified M. tuberculosis DNA were co-amplified in an SDA reaction with 25,000 copies of the synthetic internal control sequence (SEQ ID NO: 1). Following SDA, dual detection of products by chemiluminescence was performed as above. FIG. 4 presents the results. The data for the Mtb signals are presented as bars, while the internal control for the corresponding reaction is shown as a closed circle. The data for the internal controls are fitted to a line by linear regression analysis. While occasional tubes showed slightly higher or lower internal control levels, the overall trend is remarkably consistent, regardless of the initial ratio of control sequence to target sequence.

What is claimed is:

1. A method for detecting inhibition of a nucleic acid amplification reaction comprising:

a) coamplifying in the isothermal nucleic acid amplification reaction a known amount of an internal control nucleotide sequence and a target nucleotide sequence, if present, the internal control sequence exhibiting minimal secondary structure at a selected temperature for isothermal amplification and having substantially the same length and substantially the same G+C content as the target sequence, and;

b) detecting inhibition of the isothermal nucleic acid amplification reaction by detecting inhibition of amplification of the internal control nucleotide sequence.

2. The method of claim 1 wherein coamplification is by a method selected from the group consisting of SDA, 3SR and Qβ replicase amplification.

3. The method of claim 2 wherein a *M. tuberculosis* target sequence is coamplified with an internal control sequence by SDA.

4. The method of claim 1 wherein coamplification is by a method selected from the group consisting of SDA, 3SR and Qβ replicase amplification.

5. The method of claim 4 wherein a *M. tuberculosis* target sequence is coamplified with the internal control sequence by SDA.

6. A method for quantitating a pre-amplification amount of a target nucleotide sequence in a sample comprising:

a) coamplifying the target sequence, if present, and a known pre-amplification amount of an internal control nucleotide sequence in an isothermal nucleic acid amplification reaction, the internal control sequence having minimal secondary structure at a selected temperature for isothermal amplification and having substantially the same length and substantially the same G+C content as the target sequence, thereby producing a amplification products of the internal control sequence and the target sequence, if present;

b) determining a post-amplification amount of the internal control sequence and a post-amplification amount of the target sequence, and;

c) determining the pre-amplification amount of the target sequence using the post-amplification amount of the internal control sequence and the post-amplification amount of the target sequence.

7. The method of claim 6 wherein the pre-amplification amount of the target nucleotide sequence is determined by comparing a ratio of the post-amplification amount of the internal control sequence and the post-amplification amount of the target sequence to a standard curve.

8. The method of claim 7 wherein the ratio is compared to a standard curve of ratio versus initial target levels.

9. The method of claim 1 wherein inhibition is detected using a ratio of amplified target sequence and amplified internal control nucleotide sequence.

10. The method of claim 9 wherein a minimum value of the ratio indicating positivity is determined from a standard curve.

* * * * *

UNITED STATES PATENT AND TRADEMARK OFFICE
CERTIFICATE OF CORRECTION

PATENT NO. : 5,840,487
DATED : November 24, 1998
INVENTOR(S) : James G. Nadeau and Michael C. Little It is certified that error appears in the above-identified patent and that said Letters Patent is hereby corrected as shown below:

On the title page, item[*] :

delete "5,457,024' and insert --5,457,027--.

Signed and Sealed this

Sixth Day of July, 1999

Attest:

Q. TODD DICKINSON

*Attesting Officer*     *Acting Commissioner of Patents and Trademarks*